United States Patent
Schmitt et al.

(10) Patent No.: US 7,521,578 B2
(45) Date of Patent: Apr. 21, 2009

(54) PROCESS FOR THE PREPARATION OF (METH)ACRYLATES OF TETRA- OR POLYHYDRIC ALCOHOLS

(75) Inventors: Bardo Schmitt, Mainz (DE); Joachim Knebel, Alsbach-Haehnlein (DE); Guenther Graeff, Alsbach-Haehnlein (DE)

(73) Assignee: Evonik Roehm GmbH, Darmstadt (DE)

( * ) Notice: Subject to any disclaimer, the term of this patent is extended or adjusted under 35 U.S.C. 154(b) by 0 days.

(21) Appl. No.: 11/995,406

(22) PCT Filed: Aug. 16, 2006

(86) PCT No.: PCT/EP2006/065366

§ 371 (c)(1),
(2), (4) Date: Jan. 11, 2008

(87) PCT Pub. No.: WO2007/031384

PCT Pub. Date: Mar. 22, 2007

(65) Prior Publication Data

US 2008/0194861 A1    Aug. 14, 2008

(30) Foreign Application Priority Data

Sep. 15, 2005   (DE) .................. 10 2005 044 250

(51) Int. Cl.
*C07C 67/30*    (2006.01)

(52) U.S. Cl. .................................................... 560/217
(58) Field of Classification Search ............... 560/217
See application file for complete search history.

(56) References Cited

FOREIGN PATENT DOCUMENTS

| DE | 34 23 443 | 1/1986 |
|----|-----------|--------|
| EP | 0 151 368 | 8/1985 |
| EP | 0 663 386 | 7/1995 |

OTHER PUBLICATIONS

U.S. Appl. No. 11/995,406, filed Jan. 11, 2008, Schmitt, et al.
U.S. Appl. No. 12/093,744, filed May 15, 2008, Schmitt, et al.
U.S. Appl. No. 12/088,093, filed Mar. 26, 2008, Schmitt, et al.
U.S. Appl. No. 12/092,507, filed May 2, 2008, Klesse, et al.
U.S. Appl. No. 61/014,927, filed Dec. 19, 2007, Karnbrock.
U.S. Appl. No. 12/159,871, filed Jul. 2, 2008, Wiesler, et al.

*Primary Examiner*—Jafar Parsa
(74) *Attorney, Agent, or Firm*—Oblon, Spivak, McClelland, Maier & Neustadt, P.C.

(57) ABSTRACT

Process for the preparation of acrylic and methacrylic acid esters by transesterification of (meth)acrylic acid esters of the formula I: where $R_1$ is H or $CH_3$ and $R_2$ is an alkyl radical having 1 to 40 carbon atoms, with alkanols which have four or more esterifiable hydroxyl groups, characterized in that 0.01 to 10% by weight, based on the total reaction mixture, of lithium amide catalysts are used as transesterification catalyst.

16 Claims, No Drawings

PROCESS FOR THE PREPARATION OF (METH)ACRYLATES OF TETRA- OR POLYHYDRIC ALCOHOLS

The invention relates to a process for transesterifying (meth)acrylic esters with especially polyfunctional alkanols using a catalyst.

The use of diorganyltin oxides or of organyltin halides as transesterification catalysts is known. For example, DE-B 1005947 states that di- and triorganotin compounds effectively catalyse esterification and transesterification reactions of (meth)acrylic acid and (meth)acrylic esters. The advantageous effects of the catalysts described there include high catalytic activity, low tendency to dehydration, especially of secondary alcohols, and high ester yields.

The preparation of tetra- or polyfunctional (meth)acrylic esters by transesterifying (meth)acrylic esters which have small ester radicals, for example alkyl radicals, with tetra- or polyfunctional alcohols with catalysis by diorganyltin oxides or diorganyltin halides according to the prior art processes often proceeds with unsatisfactorily low conversions of the reactants within acceptable reaction times. This is the case especially for the reaction of (meth)acrylic esters with polyfunctional alcohols.

EP 663386 describes a process for transesterifying (meth)acrylic esters with especially polyfunctional alkanols using a mixed catalyst consisting of diorganyltin oxide and organyltin halide.

For example, EP 663386 specifies a reaction time of 14 hours for preparing pentaerythrityl tetramethacrylate. In addition, only 78 mol % of pentaerythrityl tetramethacrylate is isolated.

It is an object of the invention to provide a process for transesterifying (meth)acrylic esters with especially polyfunctional alkanols using a catalyst, which can prepare reaction products in acceptable purities within acceptable reaction times.

The object is achieved by a process for preparing acrylic and methacrylic esters by transesterifying (meth)acrylic esters of the formula I:

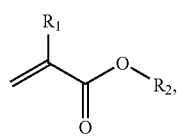

(I)

where $R_1$ is H or $CH_3$ and $R_2$ is an alkyl radial having 1 to 6 carbon atoms with alkanols which have four or more esterifiable hydroxyl groups, characterized in that the transesterification catalyst used is 0.01 to 10% by weight, based on the entire reaction mixture, of lithium amide catalysts.

It has been found that, surprisingly, the use of a catalyst from the group of the lithium amide catalysts allows the reaction times in the transesterification with higher-functionality alkanols to be shortened considerably.

It has additionally been found that it is possible using the process to prepare higher-value (meth)acrylic esters in substantially improved purities.

The notation (meth)acrylate represents the esters of (meth) acrylic acid and here means both methacrylate, for example methyl methacrylate, ethyl methacrylate, etc., and acrylate, for example methyl acrylate, ethyl acrylate, etc., and mixtures of the two.

It has been found that catalysts from the group of the lithium amides can be used preferentially.

The alkanols used in the transesterification preferably have four or more esterifiable hydroxyl groups, for example pentaerythritol, erythritol or threitol.

Particular preference is given to using tetrafunctional alkanols of the formula II:

$$R'''(OH)_n \qquad \qquad II$$

where
$n \geq 4$ and
$R'''$ is an unbranched or branched, aliphatic or aromatic radical having 4 to 40 carbon atoms.

Examples of representatives of penta- and hexafunctional alkanols which can be used as transesterification components include: arabinitol, ribitol, xylitol, sorbitol, glucitol and mannitol, all known as sugar alcohols (cf., for example, Kirk-Othmer, Encyclopedia of Chemical Technology, 3rd Ed., Vol. 1, pages 754 to 789, John Wiley, New York, 1978).

The acrylic or methacrylic esters of the formula I used may, for example, be: alkyl (meth)acrylates of straight-chain, branched or cycloaliphatic alcohols having from 1 to 40 carbon atoms, for example, methyl(meth)acrylate, ethyl(meth) acrylate, n-butyl(meth)acrylate, i-butyl(meth)acrylate, tert-butyl(meth)acrylate, pentyl(meth)acrylate, 2-ethylhexyl (meth)acrylate, stearyl(meth)acrylate, lauryl(meth)acrylate, cyclohexyl(meth)acrylate, isobornyl(meth)acrylate; aryl (meth)acrylates, for example benzyl(meth)acrylate or phenyl (meth)acrylate, each of which may have unsubstituted or mono- to tetrasubstituted aryl radicals; other aromatically substituted (meth)acrylates, for example naphthyl(meth) acrylate; mono(meth)acrylates of ethers, polyethylene glycols, polypropylene glycols or mixtures thereof having 5-80 carbon atoms, for example tetrahydrofurfuryl methacrylate, methoxy(m)ethoxyethyl methacrylate, 1-butoxypropyl methacrylate, cyclohexyloxymethyl methacrylate, benzyloxymethyl methacrylate, furfuryl methacrylate, 2-butoxyethyl methacrylate, 2-ethoxyethyl methacrylate, allyloxymethyl methacrylate, 1-ethoxybutyl methacrylate, 1-ethoxyethyl methacrylate, ethoxymethyl methacrylate, poly(ethylene glycol) methyl ether(meth)acrylate and poly (propylene glycol) methyl ether(meth)acrylate.

The reaction of acrylic or methacrylic esters of the formula I with the tetra- or polyfunctional alkanols is carried out in the presence of 0.01 to 10% by weight of catalyst, preferably of 0.1 to 5% by weight, more preferably of 0.2 to 2% by weight of catalyst, based on the overall reaction mixture.

The reaction of acrylic or methacrylic esters of the formula I with the tetra- or polyfunctional alkanols is carried out at temperatures between 30 and 180° C., preferably between 50 and 130 degrees in the presence of 0.01 to 10% by weight, preferably of 0.1 to 5% by weight, more preferably of 0.2 to 2% by weight, based on the overall reaction mixture, of the lithium amide catalyst.

The process may be carried out in any inert aprotic solvent. Preference is given to aliphatic or aromatic solvents, particular preference to xylene, toluene or cyclohexane.

In the transesterification of the compound(s) of the formula I with the alkanols, inhibitors which prevent free-radical polymerization of the (meth)acrylic groups during the reaction may be added. These inhibitors are widely known in the technical field.

Mainly 1,4-dihydroxybenzenes are used. However, differently substituted dihydroxybenzenes are also used. In general, such inhibitors can be represented by the general formula (III)

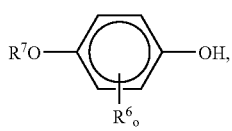

where

R[6] is a linear or branched alkyl radical having one to eight carbon atoms, halogen or aryl, preferably an alkyl radical having one to four carbon atoms, more preferably methyl, ethyl, n-propyl, isopropyl, n-butyl, isobutyl, sec-butyl, tert-butyl, Cl, F or Br;

o is an integer in the range from one to four, preferably one or two; and

R[7] is hydrogen, a linear or branched alkyl radical having one to eight carbon atoms or aryl, preferably an alkyl radical having one to four carbon atoms, more preferably methyl, ethyl, n-propyl, isopropyl, n-butyl, isobutyl, sec-butyl or tert-butyl.

However, it is also possible to use compounds with 1,4-benzoquinone as the base compound. These can be described by the formula (IV)

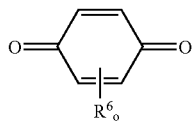

where

R[6] and o are each as defined above.

Phenols of the general structure (V) are likewise used

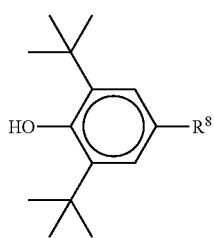

where

R[8] is a linear or branched alkyl radical having one to eight carbon atoms, aryl or aralkyl, propionic esters with mono- to tetrahydric alcohols which may also contain heteroatoms such as S, O and N, preferably an alkyl radical having one to four carbon atoms, more preferably methyl, ethyl, n-propyl, isopropyl, n-butyl, isobutyl, sec-butyl, tert-butyl.

A further advantageous class of substances is that of hindered phenols based on triazine derivatives of the formula (VI)

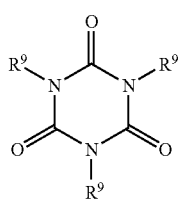

where R[9]=compound of the formula (VII)

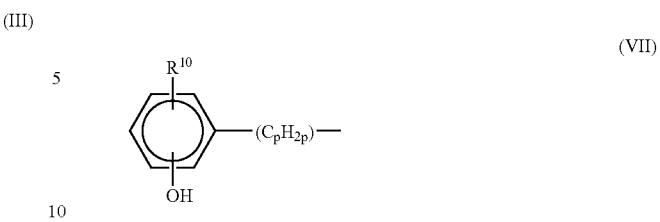

where $R^{10}=C_pH_{2p+1}$ where p=1 or 2.

Employed with particular success are the compounds 1,4-dihydroxybenzene, 4-methoxyphenol, 2,5-dichloro-3,6-dihydroxy-1,4-benzoquinone, 1,3,5-trimethyl-2,4,6-tris(3,5-di-tert-butyl-4-hydroxybenzyl)benzene, 2,6-di-tert-butyl-4-methylphenol, 2,4-dimethyl-6-tert-butylphenol, 2,2-bis[3,5-bis(1,1-dimethylethyl)-4-hydroxyphenyl-1-oxopropoxymethyl)]-1,3-propanediyl ester, 2,2'-thiodiethyl bis[3-(3,5-di-tert-butyl-4-hydroxyphenyl)]propionate, octadecyl 3- (3, 5-di-tert-butyl-4-hydroxyphenyl)propionate, 3,5-bis (1,1-dimethylethyl-2,2-methylenebis(4-methyl-6-tert-butylphenol), tris(4-tert-butyl-3-hydroxy-2,6-dimethylbenzyl)-s-triazine-2,4,6-(1H,3H,5H)-trione, tris(3, 5-di-tert-butyl-4-hydroxy)-s-triazine-2,4,6-(1H,3H, 5H)-trione or tert-butyl-3,5-dihydroxybenzene. Advantageously used are combinations of 4-hydroxy-2,2,6,6-tetramethylpiperidinooxyl, dissolved oxygen, phenothiazine, 4-(methacryloyloxy)-2,2,6,6-tetramethylpiperidine 1-oxyl, N,N-diethylhydroxylamine, N,N'-diphenyl-p-phenylenediamine or hydroquinone monomethyl ether.

Based on the weight of the overall reaction mixture, the content of the inhibitors, individually or as a mixture, is generally 0.01-0.50% (wt./wt.), the concentration of the inhibitors preferably being selected such that the colour number to DIN 55945 is not impaired. Many of these inhibitors are commercially available.

(Meth)acrylic esters of the formula I and hydroxyl groups of the tetra- or polyfunctional alkanols react to give the desired end products. In practice, it is appropriate to keep the (meth)acrylic esters I in excess during the reaction, the (meth)acrylic acid I being used in amounts of 1.2 to 15 mol, preferably 2 to 10 mol, per mole of hydroxyl groups.

The reaction can be carried out under standard pressure, reduced pressure or elevated pressure, and can be conducted batchwise or continuously. In general, the reactants (meth)acrylic ester I and tetra- or polyfunctional alkanol, are heated to reaction temperature together in the presence of the lithium amide catalyst, and the eliminated alkanol $R_2OH$ and the excess (meth)acrylic ester I are distilled off continuously, preferably together in an azeotrope. The reaction times are generally between 1 and 20 hours, preferably between 2 and 8 hours, and depend upon the reaction temperature or upon the amount of catalyst used. It is also possible to carry out the reaction in the presence of an inert solvent, for example toluene, or cyclohexane.

After the reaction has ended, the excess (meth)acrylic ester I is removed from the reaction product partly or preferably fully, for example by distilling it off. Subsequently, the removal of the catalyst is effected by filtration.

The process according to the invention for preparing (meth)acrylic esters by transesterifying (meth)acrylic esters I with tetra- or polyfunctional alkanols affords, especially in the case of preparation of polyfunctional (meth)acrylic esters, significantly higher yields and a significantly lower level of by-products than the prior art processes.

The tetra- or polyfunctional (meth)acrylic esters are outstanding copolymers for reactions in which crosslinking is desired during the polymerization. For example, they are used in coatings, dental applications, adhesives, in vulcanization or radiative curing.

The examples given below are given for better illustration of the present invention, but are not capable of restricting the invention to the features disclosed herein.

EXAMPLES

Example 1

Apart from lithium amide, the batch is introduced into the reaction apparatus and dewatered, then the batch is cooled. At approx. 80° C., lithium amide is added and the reaction temperature is increased again. The methanol formed is distilled as the MMA/methanol azeotrope through a column head. Once the column head temperature no longer falls, the reaction is ended after a reaction time of 6.7 h and at a reaction temperature of 101° C. to 113° C.

The crude product obtained is filtered and subsequently concentrated on a rotary evaporator (80° C./12 mbar) to obtain 193.8 g (=95% of theory) of a clear viscous liquid which solidifies in the course of cooling to a soft crystalline mass.

Batch:
500.5 g=5.0 mol of methyl methacrylate
68.1 g=0.5 mol of pentaerythritol
0.041 g=200 ppm based on product of hydroquinone monomethyl ether
0.41 g=0.2% based on product of lithium amide Purity:
82 mol % of pentaerythrityl tetramethacrylate
15% mol % of pentaerythrityl trimethacrylate
<1% mol % of pentaerythrityl dimethacrylate
<1% mol % of pentaerythrityl monomethacrylate
>1% mol % of monomers with functionality >4

Comparative Example 1

Pentaerythrityl Tetramethacrylate

Procedure as described in Example 1, except using 136 g (1.0 mol) of pentaerythritol, 1000 g (10.0 mol) of methyl methacrylate, 5.0 g (0.02 mol) of dibutyltin oxide and 6.1 g (0.02 mol) of dibutyltin dichloride as a mixed catalyst, and also 0.57 g of hydroquinone monomethyl ether. After 14 hours of reaction time, the excess methyl methacrylate is removed under reduced pressure. The H NMR spectroscopy analysis of the reaction product shows the following composition:
78 mol % of pentaerythrityl tetramethacrylate
18 mol % of pentaerythrityl trimethacrylate
3 mol % of pentaerythrityl dimethacrylate
1 mol % of pentaerythrityl monomethacrylate Comparative Example 2

Preparation of Pentaerythrityl Tetramethacrylate with Sole Use of Dibutyltin Dichloride as the Catalyst Procedure as described in Comparative Example 1, except using 11.4 g (0.038 mol) of dibutyltin dichloride as the catalyst. After 3.5 hours of reaction time, still no methanol has formed, i.e. no transesterification takes place.

The invention claimed is:

1. Process for preparing an acrylic or methacrylic ester comprising transesterifying a (meth)acrylic ester of the formula I:

where $R_1$ is H or $CH_3$ and $R_2$ is an alkyl radical having 1 to 40 carbon atoms, an aromatic radical, an ether radical, or a polyether radical, with an alkanol which has four or more esterifiable hydroxyl groups, in the presence of a transesterification catalyst, wherein the transesterification catalyst used is 0.01 to 10% by weight, based on the entire reaction mixture, of a lithium amide catalyst.

2. Process according to claim 1, wherein the catalyst is used in amounts of 0.1 to 5% by weight based on the overall reaction mixture.

3. Process according to claim 1, wherein the alkanol having four or more esterifiable hydroxyl groups is selected from the group of:
tetrafunctional alkanols of the formula II:

$$R'''(OH)_n \qquad \text{II}$$

where
$n \geq 4$ and
R''' is an unbranched or branched, aliphatic or aromatic radical having 4 to 40 carbon atoms.

4. Process according to claim 1, wherein the (meth)acrylic ester of the formula I is used in amounts of 1.2 to 15 mol per mole of esterifiable hydroxyl groups.

5. Process according to claim 1, wherein the transesterification reaction is carried out at temperatures between 50 and 130° C.

6. Process according to claim 1, wherein the catalyst is used in amounts of 0.2 to 2% by weight based on the overall reaction mixture.

7. Process according to claim 1, wherein the (meth)acrylic ester of the formula I is used in amounts of 2 to 10 mol per mole of esterifiable hydroxyl groups.

8. Process according to claim 1, which is carried out in the presence of a free radical polymerization inhibitor.

9. Process according to claim 1, wherein the alkanol is a penta- or hexa-functional alkanol.

10. Process according to claim 1, wherein the alkanol is a sugar alcohol.

11. Process according to claim 1, wherein the alkanol is arabinitol, ribitol, xylitol, sorbitol, glucitol or mannitol.

12. Process according to claim 1, wherein the alkanol is pentaerythritol, erythritol or threitol.

13. Process according to claim 1, which is carried out in the presence of an inert aprotic solvent.

14. Process according to claim 1, which is carried out in the presence of xylene, toluene or cyclohexane.

15. Process according to claim 1, wherein the (meth) acrylic ester of formula I comprises methyl methacrylate.

16. Process according to claim 8, wherein the (meth) acrylic ester of formula I comprises methyl methacrylate, the alkanol comprises pentaerythritol, and the inhibitor comprises hydroquinon monomethyl ether.

* * * * *